US012806193B2

(12) United States Patent
Chen et al.

(10) Patent No.: US 12,806,193 B2
(45) Date of Patent: Nov. 24, 2026

(54) PHARMACEUTICAL COMPOSITION COMPRISING THIRD GENERATION SMALL MOLECULE EGFR INHIBITOR AND PREPARATION METHOD THEREOF

(71) Applicant: Jiangsu Hansoh Pharmaceutical Group Co., LTD., Lianyungang (CN)

(72) Inventors: Weiqi Chen, Lianyungang (CN); Junjun Zhao, Lianyungang (CN); Xiaolei Wang, Lianyungang (CN); Baoqing Yin, Lianyungang (CN); Xiao Chen, Lianyungang (CN)

(73) Assignee: Jiangsu Hansoh Pharmaceutical Group Co., LTD., Lianyungang (CN)

(*) Notice: Subject to any disclaimer, the term of this patent is extended or adjusted under 35 U.S.C. 154(b) by 0 days.

(21) Appl. No.: 17/875,811

(22) Filed: Jul. 28, 2022

(65) Prior Publication Data

US 2022/0370448 A1 Nov. 24, 2022

Related U.S. Application Data

(63) Continuation of application No. 17/053,605, filed as application No. PCT/CN2019/086569 on May 13, 2019, now abandoned.

(30) Foreign Application Priority Data

May 15, 2018 (CN) ........................ 201810463668.8

(51) Int. Cl.

| | |
|---|---|
| ***A61K 31/506*** | (2006.01) |
| ***A61K 9/16*** | (2006.01) |
| ***A61K 9/20*** | (2006.01) |
| ***A61K 47/02*** | (2006.01) |
| ***A61K 47/10*** | (2017.01) |
| ***A61K 47/12*** | (2006.01) |
| ***A61K 47/26*** | (2006.01) |
| ***A61K 47/32*** | (2006.01) |
| ***A61K 47/36*** | (2006.01) |
| ***A61K 47/38*** | (2006.01) |

(52) U.S. Cl.

CPC .......... *A61K 31/506* (2013.01); *A61K 9/1694* (2013.01); *A61K 9/2095* (2013.01); *A61K 47/02* (2013.01); *A61K 47/10* (2013.01); *A61K 47/12* (2013.01); *A61K 47/26* (2013.01); *A61K 47/32* (2013.01); *A61K 47/36* (2013.01); *A61K 47/38* (2013.01)

(58) Field of Classification Search

CPC .. A61K 31/506; A61K 9/1694; A61K 9/2095; A61K 47/02; A61K 47/10; A61K 47/12; A61K 47/26; A61K 47/32; A61K 47/36; A61K 47/38

See application file for complete search history.

(56) References Cited

U.S. PATENT DOCUMENTS

| | | | | |
|---|---|---|---|---|
| 3,609,152 | A | 9/1971 | Hess et al. | |
| 4,337,341 | A | 6/1982 | Zimmerman | |
| 8,946,235 | B2 | 2/2015 | Butterworth et al. | |
| 9,796,712 | B2 | 10/2017 | Huang et al. | |
| 10,259,820 | B2 | 4/2019 | Wei et al. | |
| 10,759,782 | B2 | 9/2020 | Chen et al. | |
| 2006/0257476 | A1* | 11/2006 | Martino | A61K 9/2054 424/464 |
| 2017/0008889 | A1 | 1/2017 | Lan et al. | |
| 2017/0166598 | A1 | 6/2017 | Huang et al. | |
| 2017/0313714 | A1 | 11/2017 | Wei et al. | |
| 2017/0355696 | A1 | 12/2017 | Jiang | |
| 2017/0362204 | A1 | 12/2017 | Gray et al. | |
| 2018/0207100 | A1* | 7/2018 | Ibrahim | A61K 9/2009 |
| 2018/0208581 | A1 | 7/2018 | Zhu et al. | |
| 2019/0077791 | A1* | 3/2019 | Chen | A61P 35/00 |

FOREIGN PATENT DOCUMENTS

| | | | |
|---|---|---|---|
| CN | 103501612 | A | 1/2014 |
| CN | 103702990 | A | 4/2014 |
| CN | 104140418 | A | 11/2014 |
| CN | 104761544 | A | 7/2015 |
| CN | 104860941 | A | 8/2015 |
| CN | 105085489 | A | 11/2015 |
| JP | H-9316005 | A | 12/1997 |
| JP | 2002517430 | A | 6/2002 |
| JP | 2017502062 | A | 1/2017 |
| JP | 2017517535 | A | 6/2017 |
| WO | WO-9963970 | A1 | 12/1999 |
| WO | 2011140338 | A1 | 11/2011 |
| WO | 2013169401 | A1 | 11/2013 |
| WO | 2015175632 | A1 | 11/2015 |

(Continued)

OTHER PUBLICATIONS

Miyamoto, Hiroto. "The Particle Design of Cellulose and the Other Excipients for a Direct Compressible Filler-Binder." KONA Powder and Particle Journal, 2008, 26: 142-152. (Year: 2008).*

(Continued)

*Primary Examiner* — Doan T Phan

(74) *Attorney, Agent, or Firm* — Goodwin Procter LLP

(57) ABSTRACT

A pharmaceutical composition comprising a small molecule EGFR inhibitor and a preparation method therefor, the composition comprising N-(5-((4-(1-cyclopropyl-1H-indol-3-yl)pyrimidin-2-yl)amino)-2-((2-(dimethylamino)ethyl)(methyl)amino)-4-methoxyphenyl)acrylamide, an isomer, solvate, hydrate, or pharmaceutically acceptable salt thereof, or a combination thereof that acts as an active ingredient, and at least one pharmaceutically acceptable excipient.

14 Claims, No Drawings

(56) References Cited

FOREIGN PATENT DOCUMENTS

| | | | | | |
|---|---|---|---|---|---|
| WO | 2015188777 | A1 | | 12/2015 | |
| WO | 2015195228 | A1 | | 12/2015 | |
| WO | 2016029839 | A1 | | 3/2016 | |
| WO | 2016054987 | A1 | | 4/2016 | |
| WO | 2016070816 | A1 | | 5/2016 | |
| WO | WO-2016096999 | A1 | * | 6/2016 | ......... A61K 31/5377 |
| WO | 2017036263 | A1 | | 3/2017 | |
| WO | WO-2017161937 | A1 | * | 9/2017 | ........... A61K 31/506 |

OTHER PUBLICATIONS

Written Opinion of the International Searching Authority; State Intellectual Property Office of the P.R. China; International Application No. PCT/CN2019/086569; Aug. 5, 2019; 7 pages.

International Search Report; State Intellectual Property Office of the P.R. China; International Application No. PCT/CN2019/086569; Aug. 5, 2019; 6 pages.

Chinese Pharmacopoeia 2015 Edition; vol. 4; Editor: National Pharmacopoeia Commission; China Medical Science and Technology Press; 6 pages.

Brittain et al, "Polymorphism in Pharmaceutical Solids," vol. 192, 2nd Ed. (2009).

Byrn et al, "Solid-State Chemistry to Drugs," 2nd Ed. (1999).

Mullin et al, "Programmed cooling of batch crystallizers," Chemical Engineering Science, vol. 26, pp. 369-377 (1971).

International Search Report issued Mar. 28, 2017 in International Application No. PCT/CN2016/111717.

Berge et al. J. of Pharmaceutical Sciences, vol. 66, p. 1-19 (Year: 1977).

International Search Report issued Jan. 11, 2016 in Int'l Application No. PCT/CN2015/091189.

Ciardiello et al., "EGFR Antagonist in Cancer Treatment," The New England Journal of Medicine, vol. 358, pp. 1160-1174 (2008).

Roskoski et al, "The ErbB/HER Receptor Protein-Tyrosine Kinases and Cancer," Biochemical and Biophysical Research Communications, vol. 319, pp. 1-11 (2004).

Paez et al, "EGFR Mutations in Lung Cancer: Correlation with Clinical Response to Gefitinib Therapy," Science, vol. 304, pp. 1497-1500 (2004).

Lynch et al, "ActiPatent Annuity Remindervating Mutations in the Epidermal Growth Factor Receptor Underlying Responsiveness of Non-Small-Cell Lung Cancer to Gefitinib," The New England Journal of Medicine, vol. 350, No. 21, pp. 2129-2139 (May 20, 2004).

Finlay et al, "Discovery of a Potent and Selective EGFR Inhibitor (AZD9291) of Both Sensitizing and T790M Resistance Mutations That Spares the Wild Type Form of the Receptor," Journal of Medicinal Chemistry, vol. 57, No. 20, pp. 8249-8267 (2014).

* cited by examiner

PHARMACEUTICAL COMPOSITION COMPRISING THIRD GENERATION SMALL MOLECULE EGFR INHIBITOR AND PREPARATION METHOD THEREOF

CROSS-REFERENCE TO RELATED APPLICATIONS

This application is a continuation of U.S. patent application Ser. No. 17/053,605, filed on Nov. 6, 2020, which is a U.S. National Phase of International PCT Application No. PCT/CN2019/086569 filed May 13, 2019, which claims priority to Chinese Patent Application Serial No. 201810463668.8 filed May 15, 2018, the contents of each application are incorporated herein by reference in their entirety.

FIELD OF THE INVENTION

The present invention belongs to the field of pharmaceutical formulations, and specifically relates to a pharmaceutical composition comprising a third-generation small molecule EGFR inhibitor and a method for preparing the same.

BACKGROUND OF THE INVENTION

EGFR (Epidermal Growth Factor Receptor) is a member of the erbB receptor family, which includes transmembrane protein tyrosine kinase receptors. By binding to its ligand, such as epidermal growth factor (EGF), EGFR can form a homodimer on the cell membrane or form a heterodimer with other receptors in the family, such as erbB2, erbB3, or erbB4. The formation of these dimers can cause the phosphorylation of key tyrosine residues in EGFR cells, thereby activating a number of downstream signaling pathways in cells. These intracellular signaling pathways play an important role in cell proliferation, survival and anti-apoptosis. Disorders of EGFR signal transduction pathways, including increased expression of ligands and receptors, EGFR gene amplification and mutation and the like, can promote malignant transformation of cells, and play an important role in tumor cell proliferation, invasion, metastasis and angiogenesis. Therefore, EGFR is a reasonable target for the development of anticancer drugs N-(5-((4-(1-cyclopropyl-TH-indol-3-yl)pyrimidin-2-yl)amino)-2-((2-(dimethylamino)ethyl)(methyl)amino)-4-methoxyphenyl)acrylamide, which belongs to the third generation small molecule EGFR inhibitors, has high selectivity for inhibiting the EGFR T790M mutant, while has no or low activity on wild-type EGFR. Therefore, it can be used in treating drug-resistant tumors caused by secondary mutations of EGFR T790M. This compound was first disclosed in the international patent application WO2016054987; its structure is as shown in the following formula I, and it is hereinafter referred to as the compound of formula I:

(I)

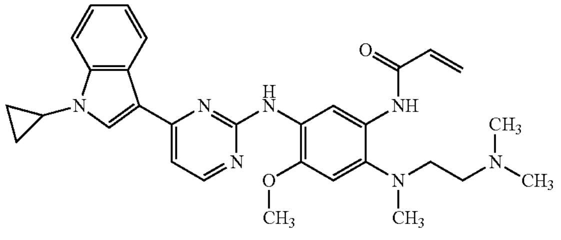

SUMMARY OF THE INVENTION

The present invention provides a pharmaceutical composition comprising a third generation small molecule EGFR inhibitor.

The pharmaceutical composition comprises a mesylate salt of N-(5-((4-(1-cyclopropyl-1H-indol-3-yl)pyrimidin-2-yl)amino)-2-((2-(dimethylamino)ethyl)(methyl)amino)-4-methoxyphenyl)acrylamide, a polymorph, solvate, hydrate, pharmaceutically acceptable salt thereof or a combination thereof as the active ingredient, and at least one pharmaceutically acceptable excipient.

In the pharmaceutical composition according to the present invention, the active ingredient is present in an amount of 1 to 60%.

In the pharmaceutical composition according to the present invention, the unit dose of the active ingredient is 10 to 200 mg, preferably 55 to 110 mg, and more preferably 55 mg or 110 mg.

In the pharmaceutical composition according to the present invention, the excipient comprises one or more filler(s), comprising at least one disaccharide or polysaccharide, such as glucan, starch, cellulose, lactose, maltose or sucrose. The starch can be selected from the group consisting of potato starch, corn starch, rice starch, wheat starch, amylopectin, pregelatinized starch and the like. The disaccharide or polysaccharide is present in an amount of 1 to 60%, preferably 5 to 55%, more preferably 5 to 30%, and further preferably 5 to 15%.

The filler is preferably a disaccharide, such as lactose, and it is present in an amount of 1 to 60%, preferably 5 to 55%, more preferably 5 to 30%, and further preferably 5 to 15%.

In the pharmaceutical composition according to the present invention, the excipient comprises one or more filler(s), disintegrant(s) or lubricant(s).

In the pharmaceutical composition according to the present invention, the weight percentage of each component is as follows:

| | |
|---|---|
| active ingredient | 1 to 60% |
| filler | 20 to 80% |
| disintegrant | 1 to 30% |
| lubricant | 0.1 to 10%. |

Preferably, the weight percentage of each component is as follows:

| | |
|---|---|
| active ingredient | 35 to 50% |
| filler | 30 to 50% |
| disintegrant | 10 to 20% |
| lubricant | 0.5 to 5%. |

More preferably, the weight percentage of each component is as follows:

| | |
|---|---|
| active ingredient | 43.3% |
| filler | 30% |
| disintegrant | 10.2% |
| lubricant | 2.5%. |

In the pharmaceutical composition according to the present invention, the filler comprises one or more of microcrystalline cellulose, lactose, anhydrous lactose, corn starch, pregelatinized starch, mannitol, sorbitol, calcium hydrophosphate and calcium sulfate, where the filler is present in an amount of 20 to 80%, and preferably 30 to 50%. Preferably, the filler comprises two of the above components, and the weight ratio of the two components is 1:3 to 3:1.

In the pharmaceutical composition according to the present invention, the filler is preferably microcrystalline cellulose and lactose. The microcrystalline cellulose is present in an amount of 1 to 60%, preferably 10 to 40%, and more preferably 20 to 40%, relative to the weight of the tablet core; and the lactose is present in an amount of 1 to 60%, preferably 5 to 30%, and more preferably 5 to 15%, relative to the weight of the tablet core. Optional technical solutions include, but are not limited to, the microcrystalline cellulose is present in an amount of 1 to 60%, and the lactose is present in an amount of 1 to 60%; the microcrystalline cellulose is present in an amount of 10 to 40%, and the lactose is present in an amount of 5 to 30%; and the microcrystalline cellulose is present in an amount of 20 to 40%, and the lactose is present in an amount of 5 to 15%.

Further preferably, the weight ratio of microcrystalline cellulose to lactose is 1:3 to 3:1, and more preferably 2-3:1.

Further preferably, the lactose is anhydrous lactose. The microcrystalline cellulose is present in an amount of 1 to 60%, preferably 10 to 40%, and more preferably 20 to 40%, relative to the weight of the tablet core; and the anhydrous lactose is present in an amount of 1 to 60%, preferably 5 to 30%, and more preferably 5 to 15%, relative to the weight of the tablet core. Optional technical solutions include, but are not limited to, the microcrystalline cellulose is present in an amount of 1 to 60%, and the anhydrous lactose is present in an amount of 1 to 60%; the microcrystalline cellulose is present in an amount of 10 to 40%, and the anhydrous lactose is present in an amount of 5 to 30%; and the microcrystalline cellulose is present in an amount of 20 to 40%, and the anhydrous lactose is present in an amount of 5 to 15%.

Further preferably, the weight ratio of microcrystalline cellulose to anhydrous lactose is 1:3 to 3:1, more preferably 2-3:1.

Through the addition of lactose, the pharmaceutical composition with a high content of the compound of formula I can be prepared, and its drug loading capacity can reach more than 40%. At the same time, the resulting pharmaceutical composition has a good compressibility and uniform dissolution.

In the pharmaceutical composition according to the present invention, the disintegrant comprises one or more of low-substituted hydroxypropyl cellulose, croscarmellose sodium, carboxymethyl starch sodium and crospovidone, and preferably carboxymethyl starch sodium. The disintegrant is present in an amount of 1 to 30%, and preferably 10 to 20%. The disintegrant that is added in a totally intragranular manner can ensure good disintegration and preparation of the tablet. The addition of carboxymethyl starch sodium can further improve the stability of the formulation. Preferably, the disintegrant is added intragranularly.

In the pharmaceutical composition according to the present invention, the lubricant comprises one or more of talc, stearic acid, sodium stearyl fumarate, glyceryl behenate, magnesium stearate and micronized silica gel. The lubricant is present in an amount of 0.1 to 10%, and preferably 0.2 to 5%, relative to the weight of the tablet core.

Further, the lubricant is preferably sodium stearyl fumarate and magnesium stearate. The sodium stearyl fumarate is present in an amount of 0.1 to 5%, and preferably 0.3 to 3%, and the magnesium stearate is present in an amount of 0.1 to 5%, and preferably 0.2 to 2%. The combination of sodium stearyl fumarate and magnesium stearate can obviously improve the adhesion of raw materials on the surface of the equipment, ensure a smooth preparation process, and enable the finished product to have an excellent dissolution effect.

In the pharmaceutical composition according to the present invention, the amount refers to the percentage relative to the total weight of the drug, wherein the total weight of the drug does not include the weight of the coating. As for specific dosage forms, the amount refers to the percentage relative to the weight of the tablet core or granule.

The pharmaceutical composition according to the present invention comprises the following components:

| | |
|---|---|
| active ingredient | 35 to 50% |
| lactose | 5 to 15% |
| microcrystalline cellulose | 30 to 50% |
| carboxymethyl starch sodium | 10 to 20% |
| lubricant | 0.5 to 5%. |

Preferably, it comprises the following components:

| | |
|---|---|
| active ingredient | 43.3% |
| lactose | 10.2% |
| microcrystalline cellulose | 30% |
| carboxymethyl starch sodium | 10.4% |
| lubricant | 0.5 to 5%. |

More preferably, it comprises the following components:

| | |
|---|---|
| active ingredient | 43.3% |
| lactose | 10.2% |
| microcrystalline cellulose | 30% |
| carboxymethyl starch sodium | 14% |
| lubricant | 2.5%. |

Most preferably, it comprises the following components:

| | |
|---|---|
| active ingredient | 43.3% |
| lactose | 10.2% |
| microcrystalline cellulose | 30% |
| carboxymethyl starch sodium | 14% |
| magnesium stearate | 1% |
| sodium stearyl fumarate | 1.5% |

The pharmaceutical composition of the present invention is an oral formulation selected from the group consisting of tablet and capsule, preferably a film, and more preferably an immediate-release film-coated tablet. The coating agent is a gastric-soluble film coating premix, preferably Opadry 85F140124 (the main ingredients are polyvinyl alcohol, polyethylene glycol, talc, titanium dioxide, iron oxide red and iron oxide black), and Opadry 85F12300 (the main ingredients are polyvinyl alcohol, polyethylene glycol, talc, titanium dioxide and iron oxide yellow).

The present invention further provides a method for preparing the pharmaceutical composition, mainly comprising the following steps of:

1) pre-treatment of raw materials: sieving the filler, disintegrant and lubricant for later use;
2) mixing: weighing the intragranular raw materials according to specified amounts and mixing them;
3) dry granulation: granulating the above mixed powder by dry granulation;

4) total mixing: mixing the resulting granules and extragranular lubricant;

5) optionally, tableting: compressing the resulting mixture into tablets according to the theoretical tablet weight; and 6) optionally, coating.

The above method comprises the specific steps of:

1) pre-treatment of raw materials: sieving microcrystalline cellulose and anhydrous lactose with a 60-mesh sieve, and sieving sodium stearyl fumarate and carboxymethyl starch sodium with an 80-mesh sieve for later use;

2) mixing: weighing the intragranular raw materials according to prescription amounts, and mixing microcrystalline cellulose, anhydrous lactose, carboxymethyl starch sodium, sodium stearyl fumarate, the active ingredient and magnesium stearate with a hopper mixer;

3) dry granulation: granulating the above mixed powder with a dry granulator; 4) total mixing: mixing the resulting fine granules and prescription amount of extragranular sodium stearyl fumarate with a hopper mixer;

5) optionally, tableting: compressing the resulting mixture into tablets according to the theoretical tablet weight; and 6) optionally, coating: i) formulation of a coating liquid, adding a prescription amount of Opadry to purified water under stirring to formulate a coating liquid with a solid content of 10%, stirring the coating liquid for 60 minutes after the completion of the addition of Opadry to make it evenly dispersed, and sieving the formulated coating liquid with a 100-mesh sieve for later use; and ii) setting the parameters according to the process requirements, and finishing the coating until the coating weight gain reaches about 2.0% to 4.0%.

The inventor finds through a large number of studies that N-(5-((4-(1-cyclopropyl-1H-indol-3-yl)pyrimidin-2-yl)amino)-2-((2-(dimethylamino)ethyl)(methyl)amino)-4-methoxyphenyl)acrylamide, as third-generation small molecule EGFR inhibitor, is a drug with low permeability. Its solubility is greatly affected by pH, which is pH dependent. The pharmaceutical composition prepared according to the present invention has a good and uniform dissolution in different dissolution media.

DETAILED DESCRIPTION OF THE INVENTION

Regarding to the Filler:

It can be found from Table 1 that when the filler comprises lactose, a pharmaceutical composition with a high content of the compound of formula I can be prepared, and the resulting pharmaceutical composition has a good compressibility.

| Single-factor study | Sample 1 | Sample 2 | Sample 3 |
|---|---|---|---|
| Active ingredient[1] | 1.416 | 1.416 | 1.416 |
| Microcrystalline cellulose | 1.05 | 1.05 | 1.05 |
| Anhydrous lactose | 3.15 | / | 1.56 |
| Mannitol | / | 3.15 | 1.59 |
| Croscarmellose sodium (added intragranularly) | 0.18 | 0.18 | 0.18 |
| Croscarmellose sodium (added extragranularly) | 0.09 | 0.09 | 0.09 |
| Magnesium stearate (added intragranularly) | 0.09 | 0.09 | 0.09 |
| Magnesium stearate (added extragranularly) | 0.084 | 0.084 | 0.084 |
| Process of compressing large tablets (called "slugs") | There was no punch sticking, and the large tablets were smooth and 100% qualified | There was punch sticking, and the large tablets were not smooth and does not meet the production requirement | There was punch sticking, and the large tablets were not smooth and does not meet the production requirement |

[1]Note:
The active ingredient is calculated by mesylate salt, the same below.

The drug loading capacity of the active ingredient in the tablet was further increased. When the active ingredient was present in an amount of 43.3%, the tablet still had a very good compressibility. There was no punch sticking. The resulting uncoated tablets were smooth and 100% qualified, having a complete shape and good appearance.

TABLE 2

The types and dosage of the filer

| Single factor study | Microcrystalline cellulose (PH102) + anhydrous lactose (21AN) Ratio: 3:1 | Ratio: 1:1 | Ratio: 1:3 |
|---|---|---|---|
| Batch | 200 tablets/g | 200 tablets/g | 200 tablets/g |
| Active ingredient [1] | 25.96 | 25.96 | 25.96 |
| Microcrystalline cellulose (PH102) | 18.00 | 12.00 | 6.00 |
| Anhydrous lactose (21AN) | 6.14 | 12.14 | 18.14 |
| Carboxymethyl starch sodium (type A) | 8.40 | 8.40 | 8.40 |
| Sodium stearyl fumarate (intragranular) | 0.3 | 0.3 | 0.3 |
| Magnesium stearate (intragranular) | 0.6 | 0.6 | 0.6 |

TABLE 2-continued

| The types and dosage of the filer | | | |
|---|---|---|---|
| | Microcrystalline cellulose (PH102) + anhydrous lactose (21AN) | | |
| Single factor study | Ratio: 3:1 | Ratio: 1:1 | Ratio: 1:3 |
| Sodium stearyl fumarate (extragranular) | 0.6 | 0.6 | 0.6 |
| Process of compressing large tablets | There was no punch sticking, and the large tablets were smooth. | There was no punch sticking, and the large tablets were smooth. | There was no punch sticking, and the large tablets were smooth. |
| Hardness of uncoated tablets (kgf) | 6.60 | 6.67 | 6.89 |

TABLE 2-continued

| The types and dosage of the filer | | | | | |
|---|---|---|---|---|---|
| | | | Microcrystalline cellulose (PH102) + anhydrous lactose (21AN) | | |
| Single factor study | | | Ratio: 3:1 | Ratio: 1:1 | Ratio: 1:3 |
| Cumulative dissolution rate (%) | 0.1 M HCl | 15 min | 90 | 83 | 89 |

[1] Note:
the active ingredient is calculated by mesylate salt, the same below.

Moreover, the hardness of uncoated tablet is also one of the factors that affect the dissolution rate. Uneven hardness may lead to uneven dissolution, thereby affecting the efficacy. Table 3 below shows the corresponding dissolution profile of the prescription of the present invention at different hardnesses. It can be seen from the table that the prescription of the present invention can eliminate the effect of hardness changes on the dissolution result of the uncoated tablet under different hardness conditions, and enable the product to maintain a good dissolution rate. Therefore, the prescription of the present invention can overcome the adverse effect caused by the different hardness of uncoated tablets.

TABLE 3

| Dissolution rate test of the prescription of the present invention at different hardnesses | | | | | | | | |
|---|---|---|---|---|---|---|---|---|
| | | | Proportion (%) | | | Prescription amount (g) | | |
| Active ingredient | | | 43.27 | | | 25.96 | | |
| Microcrystalline cellulose | | | 30.00 | | | 18.0 | | |
| Anhydrous lactose | | | 10.23 | | | 6.14 | | |
| Carboxymethyl starch sodium | | | 14.00 | | | 8.4 | | |
| Sodium stearyl fumarate (intragranular) | | | 0.50 | | | 0.3 | | |
| Magnesium stearate (intragranular) | | | 1.00 | | | 0.6 | | |
| Sodium stearyl fumarate (extragranular) | | | 1.00 | | | 0.6 | | |
| | | | Hardness range (kgf) | | | | | |
| | | | 5.50 | | 10.30 | | 6.20 | |
| Dissolution profile in 30 min | | | Almost no accumulation at the bottom of the bottle. | | Almost no accumulation at the bottom of the bottle | | Almost no accumulation at the bottom of the bottle. | |
| | | n = 6 | Average | RSD | Average | RSD | Average | RSD |
| Cumulative dissolution rate (%) | 0.1M Hydrochloric acid | 5 min | 41 | 13.1 | 36 | 5.9 | 60 | 5.3 |
| | | 15 min | 88 | 2.7 | 88 | 1.4 | 91 | 3.4 |
| | | 30 min | 90 | 1.9 | 92 | 1.2 | 93 | 2.3 |

Regarding to the Disintegrant:

In the pharmaceutical composition system of the present invention, the addition of the disintegrant can also affect the dissolution rate of the tablet. The inventor finds that the dissolution rate is good when the disintegrant is present in an amount of 1 to 30%. See Table 4 for details. Carboxymethyl starch sodium used as the disintegrant can ensure a good disintegration and preparation of the tablet, and the preferred dosage is 10% to 20

TABLE 4

Dosage and adding method of the disintegrant

| Single factor study | | | Carboxy methyl starch sodium (14%) added intragranularly | Carboxy methyl starch sodium (6%) added intragranularly | Carboxy methyl starch sodium (16%) added intragranularly | Carboxy methyl starch sodium (8%) added intragranularly | Carboxymethyl starch sodium (16%) added intragranularly: added extragranularly = 1:1 | Carboxymethyl starch sodium (14%) added intragranularly: added extragranularly = 1:1 |
|---|---|---|---|---|---|---|---|---|
| | | | Dosage and adding method of the disintegrant | | | | | |
| Batch | | | 200 tablets/g | 200 tablets/g | 200 tablets/g | 200 tablets/g | 200 tablets/g | 200 tablets/g |
| Active ingredient | | | 25.96 | 25.96 | 25.96 | 25.96 | 25.96 | 25.96 |
| Microcrystalline cellulose (PH102) | | | 18.00 | 21.6 | 17.1 | 19.8 | 17.1 | 18.0 |
| Anhydrous lactose (21AN) | | | 6.14 | 7.338 | 5.84 | 6.738 | 5.84 | 6.14 |
| Carboxymethyl starch sodium, type A (added intragranularly) | | | 8.4 | 3.6 | 9.6 | 6.0 | 4.8 | 4.2 |
| Sodium stearyl fumarate (added intragranularly) | | | 0.3 | 0.3 | 0.3 | 0.3 | 0.3 | 0.3 |
| Magnesium stearate (added intragranularly) | | | 0.6 | 0.6 | 0.6 | 0.6 | 0.6 | 0.6 |
| Carboxymethyl starch sodium, type A (added extragranularly) | | | / | / | / | / | 4.8 | 4.2 |
| Sodium stearyl fumarate (added extragranularly) | | | 0.6 | 0.6 | 0.6 | 0.6 | 0.6 | 0.6 |
| Hardness of uncoated tablets (kgf) | | | 6.60 | 6.53 | 6.53 | 6.53 | 6.44 | 6.37 |
| Cumulative dissolution rate (%) | 0.1M HCl | 15 min | 90 | 74 | 88 | 72 | 86 | 82 |

Example 1

A pharmaceutical composition comprising a mesylate salt of N-(5+(4-(1-cyclopropyl-1H-indol-3-yl)pyrimidin-2-yl) amino)-2-((2-(dimethylamino)ethyl)(methyl)amino)-4-methoxyphenyl)acrylamide comprises the components of: 64.9 mg of the active ingredient (calculated by $C_{30}H_{35}N_7O_2 \cdot CH_3SO_3H$), 45.0 mg of microcrystalline cellulose (KG802), 15.3 mg of anhydrous lactose (21AN), 21.0 mg of carboxymethyl starch sodium (type A), 0.8 mg of intragranular sodium stearyl fumarate, 1.5 mg of extragranular sodium stearyl fumarate and 1.5 mg of magnesium stearate. The prescription is as follows:

| | |
|---|---|
| Mesylate salt of the compound of formula I | 43.3% |
| Microcrystalline cellulose | 30.0% |
| Anhydrous lactose | 10.2% |
| Carboxymethyl starch sodium | 14% |
| Sodium stearyl fumarate | 0.5% + 1.0% |
| Magnesium stearate | 1.0% |

The immediate-release film-coated tablets comprising the above components are prepared by the following preparation method:

(1) Pre-Treatment of Raw Materials

| Material name | Treatment method |
|---|---|
| Microcrystalline cellulose (KG802) | Sieved with a 60-mesh sieve |
| Anhydrous lactose (21AN) | Sieved with a 60-mesh sieve |
| Carboxymethyl starch sodium (type A) | Sieved with an 80-mesh sieve |
| Sodium stearyl fumarate | Sieved with an 80-mesh sieve |

(2) Weighing The raw materials were weighed according to the schedule list.

(3) Mixing

1) Premixing I: the intragranular raw materials were mixed in a hopper mixer (speed: 15 rpm, time: 10 min). 2) Milling: sieve size: 1.0 mm, milling speed: 350 to 800 rpm. 3) Premixing II: the milled material and magnesium stearate were mixed in a hopper mixer (speed: 15 rpm, time: 10 min).

(4) Dry Granulation

Delivery frequency conversion (Hz): 7 to 13; tableting frequency conversion (Hz): 20 to 40; granulation frequency conversion (Hz): 30 to 50; granulation sieve size: 1.0 mm; powder mesh number: 60 mesh.

(5) Total Mixing

The fine granules obtained by dry granulation and a prescription amount of extragranular sodium stearyl fumarate were mixed in a hopper mixer for 10 m in at a speed of 15 rpm.

(6) Tableting

The theoretical tablet weight was calculated according to the particle content. The mixture was compressed into tablets after adjusting the tablet weight and hardness.

(7) Coating

1) Formulation of a coating liquid: a coating liquid with a solid content of 10% was formulated with a film-coating premix (gastric-soluble type) and a prescription amount of purified water. The coating liquid was stirred for 60 minutes, and filtered with a 100-mesh sieve for later use.

2) Coating: the corresponding parameters were set according to the process requirements. During the coating process, the bed temperature was controlled at 30 to 40° C., and the coating weight gain was 2.0 to 4.0%.

(8) Packaging.

Example 2

A pharmaceutical composition comprising the mesylate salt of N-(5-((4-(1-cyclopropyl-1H-indol-3-yl)pyrimidin-2-yl)amino)-2-((2-(dimethylamino)ethyl)(methyl)amino)-4-methoxyphenyl)acrylamide comprises the components of: 129.8 mg of the active ingredient (calculated by $C_{30}H_{35}N_7O_2 \cdot CH_3SO_3H$), 90.0 mg of microcrystalline cellulose (KG802), 30.6 mg of anhydrous lactose (21AN), 42.0 mg of carboxymethyl starch sodium (Type A), 1.6 mg of intragranular sodium stearyl fumarate, 3.0 mg of extragranular sodium stearyl fumarate and 3.0 mg of magnesium stearate. The prescription is as follows:

| | |
|---|---|
| Mesylate salt of the compound of formula I | 43.3% |
| Microcrystalline cellulose | 30.0% |
| Anhydrous lactose | 10.2% |
| Carboxymethyl starch sodium | 14% |
| Sodium stearyl fumarate | 0.5% + 1.0% |
| Magnesium stearate | 1.0% |

The immediate-release film-coated tablets comprising the above components were prepared by the following preparation method:

(1) Pre-Treatment of Raw Materials

| Material name | Treatment method |
|---|---|
| Microcrystalline cellulose (KG802) | Sieved with a 60-mesh sieve |
| Anhydrous lactose (21AN) | Sieved with a 60-mesh sieve |
| Carboxymethyl starch sodium (type A) | Sieved with an 80-mesh sieve |
| Sodium stearyl fumarate | Sieved with an 80-mesh sieve |

(2) Weighing The raw materials were weighed according to the schedule list.

(3) Mixing

1) Premixing I: the intragranular raw materials (microcrystalline cellulose (KG802), anhydrous lactose (2 1 AN), carboxymethyl starch sodium (Type A), sodium stearyl fumarate, the active pharmaceutical ingredient) were mixed in a hopper mixer (speed: 15 rpm, time: 20 min). 2) Premixing II: after premixing I was completed, magnesium stearate (intragranular) was added to the hopper mixer for mixing (speed: 15 rpm, time: 10 min).

(4) Dry Granulation

HFS speed: 30 to 45 rpm, VFS speed: 200 to 240 rpm, pressure wheel speed: 3 to 7 rpm, pressure wheel pressure: 20 to 25 KN, crushing knife speed: 1000 to 1500 rpm, pressure wheel gap: 1.0 mm, granulation sieve size: 1.6 mm.

(5) Total Mixing

The fine granules obtained by dry granulation and a prescription amount of extragranular sodium stearyl fumarate were mixed in a hopper mixer for 10 m in at a speed of 15 rpm.

(6) Tableting

The theoretical tablet weight was calculated according to the particle content. The mixture was compressed into tablets after adjusting the tablet weight and hardness.

(7) Coating

1) Formulation of a coating liquid: a coating liquid with a solid content of 10% was formulated with a film-coating premix (gastric-soluble type) and a prescription amount of purified water. The coating liquid was stirred for 60 minutes, and filtered with an 80-mesh sieve for later use.

2) Coating: the corresponding parameters were set according to the process requirements. During the coating process, the bed temperature was controlled at 30 to 40° C., and the coating weight gain was 2.0 to 4.0%.

(8) Packaging.

Example 3

A pharmaceutical composition comprising the mesylate salt of N-(5-(4-(1-cyclopropyl-1H-indol-3-yl)pyrimidin-2-yl)amino)-2-((2-(dimethylamino)ethyl)(methyl)amino)-4-methoxyphenyl)acrylamide comprises the components of: 5.9 mg of the active ingredient (calculated by $C_{30}H_{35}N_7O_2 \cdot CH_3SO_3H$), 25.0 mg of microcrystalline cellulose, 54.7 mg of anhydrous lactose, 15.0 mg of carboxymethyl starch sodium, 0.5 mg of intragranular sodium stearyl fumarate, 0.9 mg of extragranular sodium stearyl fumarate and 0.5 mg of magnesium stearate. The prescription is as follows:

| | |
|---|---|
| Mesylate salt of the compound of formula I | 5.8% |
| Microcrystalline cellulose | 24.4% |
| Anhydrous lactose | 53.4% |
| Carboxymethyl starch sodium | 14.6% |
| Sodium stearyl fumarate | 0.5% + 0.8% |
| Magnesium stearate | 0.5% |

The immediate-release film-coated tablets comprising the above components were prepared by the preparation method of Example 1.

Example 4

A pharmaceutical composition comprising the mesylate salt of N-(5-(4-(1-cyclopropyl-1H-indol-3-yl)pyrimidin-2-yl)amino)-2-((2-(dimethylamino)ethyl)(methyl)amino)-4-methoxyphenyl)acrylamide comprises the components of: 31.8 mg of the active ingredient (calculated by $C_{30}H_{35}N_7O_2 \cdot CH_3SO_3H$), 30.0 mg of microcrystalline cellulose, 89.4 mg of anhydrous lactose, 30.0 mg of carboxymethyl starch sodium, 1.0 mg of intragranular sodium stearyl fumarate, 1.8 mg of extragranular sodium stearyl fumarate and 1.0 mg of magnesium stearate.

The immediate-release film-coated tablets comprising the above components were prepared by the preparation method of Example 2.

| | |
|---|---|
| Mesylate salt of the compound of formula I | 17.2% |
| Microcrystalline cellulose | 16.2% |
| Anhydrous lactose | 48.3% |

-continued

| | |
|---|---|
| Carboxymethyl starch sodium | 16.2% |
| Sodium stearyl fumarate | 0.5% + 1.0% |
| Magnesium stearate | 0.5% |

Example 5

A pharmaceutical composition comprising the mesylate salt of N-(5-(4-(1-cyclopropyl-1H-indol-3-yl)pyrimidin-2-yl)amino)-2-((2-(dimethylamino)ethyl)(methyl)amino)-4-methoxyphenyl)acrylamide comprises the components of: 47.2 mg of the active ingredient (calculated by $C_{30}H_{35}N_7O_2{\cdot}CH_3SO_3H$), 30.0 mg of microcrystalline cellulose, 93 mg of anhydrous lactose, 30.0 mg of carboxymethyl starch sodium, 1.0 mg of intragranular sodium stearyl fumarate, 1.8 mg of extragranular sodium stearyl fumarate and 2.0 mg of magnesium stearate.

| | |
|---|---|
| Mesylate salt of the compound of formula I | 23.0% |
| Microcrystalline cellulose | 14.6% |
| Anhydrous lactose | 45.5% |
| Carboxymethyl starch sodium | 14.6% |
| Sodium stearyl fumarate | 0.5% + 0.9% |
| Magnesium stearate | 1.0% |

The immediate-release film-coated tablets comprising the above components were prepared by the preparation method of Example 1.

Example 6

A pharmaceutical composition comprising the mesylate salt of N-(5-((4-(1-cyclopropyl-1H-indol-3-yl)pyrimidin-2-yl)amino)-2-((2-(dimethylamino)ethyl)(methyl)amino)-4-methoxyphenyl)acrylamide comprises the components of 97.35 g of the active ingredient (calculated by $C_{30}H_{35}N_7O_2{\cdot}CH_3SO_3H$), 67.5 g of microcrystalline cellulose, 22.95 g of anhydrous lactose, 31.5 g of carboxymethyl starch sodium, 1.2 g of intragranular sodium stearyl fumarate, 2.25 g of extragranular sodium stearyl fumarate and 2.25 g of magnesium stearate.

| | |
|---|---|
| Mesylate salt of the compound of formula I | 43.3% |
| Microcrystalline cellulose | 30.0% |
| Anhydrous lactose | 10.2% |
| Carboxymethyl starch sodium | 14.0% |
| Sodium stearyl fumarate | 0.5% + 1.0% |
| Magnesium stearate | 1.0% |

The immediate-release film-coated tablets comprising the above components were prepared by the preparation method of Example 2.

Example 7

A pharmaceutical composition comprising the mesylate salt of N-(5-((4-(1-cyclopropyl-TH-indol-3-yl)pyrimidin-2-yl)amino)-2-((2-(dimethylamino)ethyl)(methyl)amino)-4-methoxyphenyl)acrylamide comprises the components of 259.6 g of the active ingredient (calculated by $C_{30}H_{35}N_7O_2{\cdot}CH_3SO_3H$), 180.0 g of microcrystalline cellulose, 61.2 g of anhydrous lactose, 84.0 g of carboxymethyl starch sodium, 3.2 g of intragranular sodium stearyl fumarate, 6.0 g of extragranular sodium stearyl fumarate and 6.0 g of magnesium stearate.

| | |
|---|---|
| Mesylate salt of the compound of formula I | 43.3% |
| Microcrystalline cellulose | 30.0% |
| Anhydrous lactose | 10.2% |
| Carboxymethyl starch sodium | 14.0% |
| Sodium stearyl fumarate | 0.5% + 1.0% |
| Magnesium stearate | 1.0% |

The immediate-release film-coated tablets comprising the above components were prepared by the preparation method of Example 1.

Example 8

A pharmaceutical composition comprising the mesylate salt of N-(5-(4-(1-cyclopropyl-1H-indol-3-yl)pyrimidin-2-yl)amino)-2-((2-(dimethylamino)ethyl)(methyl)amino)-4-methoxyphenyl)acrylamide comprises the components of 97.35 g of the active ingredient (calculated by $C_{30}H_{35}N_7O_2{\cdot}CH_3SO_3H$), 67.5 g of microcrystalline cellulose, 22.95 g of anhydrous lactose, 31.5 g of carboxymethyl starch sodium, 1.2 g of intragranular sodium stearyl fumarate, 2.25 g of extragranular sodium stearyl fumarate and 2.25 g of magnesium stearate.

| | |
|---|---|
| Mesylate salt of the compound of formula I | 43.3% |
| Microcrystalline cellulose | 30.0% |
| Anhydrous lactose | 10.2% |
| Carboxymethyl starch sodium | 14.0% |
| Sodium stearyl fumarate | 0.5% + 1.0% |
| Magnesium stearate | 1.0% |

The immediate-release film-coated tablets comprising the above components were prepared by the preparation method of Example 2.

Example 9

A pharmaceutical composition comprising the mesylate salt of N-(5-(4-(1-cyclopropyl-1H-indol-3-yl)pyrimidin-2-yl)amino)-2-((2-(dimethylamino)ethyl)(methyl)amino)-4-methoxyphenyl)acrylamide comprises the components of: 47.2 mg of the active ingredient (calculated by $C_{30}H_{35}N_7O_2CH_3SO_3H$), 30.0 mg of sorbitol, 93 mg of calcium hydrophosphate, 30.0 mg of crospovidone XL, 1.0 mg of intragranular sodium stearyl fumarate, 1.8 mg of extragranular stearic acid and 2.0 mg of talc.

| | |
|---|---|
| Mesylate salt of the compound of formula I | 23.0% |
| Sorbitol | 14.6% |
| Calcium hydrophosphate | 45.4% |
| Crospovidone | 14.6% |
| Sodium stearyl fumarate | 0.5% |
| Stearic acid | 0.9% |
| Talc | 1.0% |

The immediate-release film-coated tablets comprising the above components were prepared by the preparation method of Example 1.

Example 10

A pharmaceutical composition comprising the mesylate salt of N-(5-(4-(1-cyclopropyl-1H-indol-3-yl)pyrimidin-2-yl)amino)-2-((2-(dimethylamino)ethyl)(methyl)amino)-4-methoxyphenyl)acrylamide comprises the components of: 47.2 mg of the active ingredient (calculated by $C_{30}H_{35}N_7O_2CH_3SO_3H$), 30.0 mg of sucrose, 93 mg of calcium hydrophosphate, 30.0 mg of crospovidone XL, 1.0 mg of intragranular sodium stearyl fumarate, 1.8 mg of extragranular stearic acid and 2.0 mg of talc.

| | |
|---|---|
| Mesylate salt of the compound of formula I | 23.0% |
| Sorbitol | 14.6% |
| Calcium hydrophosphate | 45.4% |
| Crospovidone | 14.6% |
| Sodium stearyl fumarate | 0.5% |
| Stearic acid | 0.9% |
| Talc | 1.0% |

The immediate-release film-coated tablets comprising the above components were prepared by the preparation method of Example 1.

Example 11

A pharmaceutical composition comprising the mesylate salt of N-(5-((4-(1-cyclopropyl-1H-indol-3-yl)pyrimidin-2-yl)amino)-2-((2-(dimethylamino)ethyl)(methyl)amino)-4-methoxyphenyl)acrylamide comprises the components of: 97.35 g of the active ingredient (calculated by $C_{30}H_{35}N_7O_2CH_3SO_3H$), 67.5 g of microcrystalline cellulose, 22.95 g of maltose, 31.5 g of carboxymethyl starch sodium, 1.2 g of intragranular sodium stearyl fumarate, 2.25 g of extragranular sodium stearyl fumarate and 2.25 g of magnesium stearate.

| | |
|---|---|
| Mesylate salt of the compound of formula I | 43.3% |
| Microcrystalline cellulose | 30.0% |
| Maltose | 10.2% |
| Carboxymethyl starch sodium | 14.0% |
| Sodium stearyl fumarate | 0.5% + 1% |
| Magnesium stearate | 1.0% |

The immediate-release film-coated tablets comprising the above components were prepared by the preparation method of Example 2.

Example 12

A pharmaceutical composition comprising the mesylate salt of N-(5-(4-(1-cyclopropyl-1H-indol-3-yl)pyrimidin-2-yl)amino)-2-((2-(dimethylamino)ethyl)(methyl)amino)-4-methoxyphenyl)acrylamide comprises the components of: 64.9 mg of the active ingredient (calculated by $C_{30}H_{35}N_7O_2CH_3SO_3H$), 45.0 mg of microcrystalline cellulose (KG802), 15.3 mg of corn starch, 21.0 mg of carboxymethyl starch sodium (Type A), 0.8 mg of intragranular sodium stearyl fumarate, 1.5 mg of extragranular sodium stearyl fumarate and 1.5 mg of magnesium stearate. The prescription is as follows:

| | |
|---|---|
| Mesylate salt of the compound of formula I | 43.3% |
| Microcrystalline cellulose | 30.0% |
| Corn starch | 10.2% |
| Carboxymethyl starch sodium | 14.0% |
| Sodium stearyl fumarate | 0.5% + 1% |
| Magnesium stearate | 1.0% |

The immediate-release film-coated tablets comprising the above components were prepared by the preparation method of Example 1.

Stability Test and Result Analysis

1. Stability of the Product in Different Dissolution Media

Chromatography Condition

Instruments and reagents High performance liquid chromatograph, electronic analytical balance, potassium dihydrogen phosphate (chromatographically pure), acetonitrile (chromatographically pure), reference substance for system suitability of related substance.

Chromatography condition Octadecylsilane bonded silica gel as the filler (Waters XBridge C18, 4.6 mm×150 mm, 3.5 μm or a column with equivalent performance); flow rate: 1.0 ml/min; detection wavelength: 220 nm; column temperature: 35° C.; injection volume: 10 μl.

Mobile phase A 2.72 g of potassium dihydrogen phosphate was dissolved in about 900 ml of water, the pH was adjusted to 6.0 with sodium hydroxide solution, water was added until the volume reached 1000 ml, and then the solution was mixed well, filtrated and degassed.

Mobile Phase B Acetonitrile

Gradient elution was carried out according to the following table (the amount of mobile phase is scalable)

| | Time (min) | | | | | |
|---|---|---|---|---|---|---|
| | 0 | 20 | 30 | 40 | 42 | 50 |
| Mobile Phase A (%) | 80 | 60 | 30 | 30 | 80 | 80 |
| Mobile Phase A (%) | 20 | 40 | 70 | 70 | 20 | 20 |

0.05% phosphoric acid solution 0.5 ml of phosphoric acid was added to 1000 ml of water and mixed well.

Diluent 800 ml of 0.05% phosphoric acid solution and 200 ml of acetonitrile were mixed well.

TABLE 5

Results of the stability study of the product in different media

| Dissolution medium | | Time (hour) 0 hour | 1 hour | 2 hours | 4 hours | 8 hours | 24 hours |
|---|---|---|---|---|---|---|---|
| 0.1 mol/L acid solution | Peak area | 5817.502 | 5724.833 | 5715.132 | 5709.908 | 5691.358 | 5709.127 |
| hydrochloric | Relative content | 100.0% | 98.4% | 98.2% | 98.2% | 97.8% | 98.1% |
| acetate buffer, pH 4.5 | Peak area | 5388.433 | 5313.248 | 5301.212 | 5294.096 | 5282.456 | 5308.160 |
| | Relative content | 100.0% | 98.6% | 98.4% | 98.2% | 98.0% | 98.5% |
| phosphate buffer, pH 6.8 | Peak area | 3364.067 | 3310.739 | 3294.386 | 3270.577 | 3264.820 | 3236.565 |
| | Relative content | 100.0% | 98.4% | 97.9% | 97.2% | 97.0% | 96.2% |

TABLE 5-continued

Results of the stability study of the product in different media

| Dissolution medium | | Time (hour) 0 hour | 1 hour | 2 hours | 4 hours | 8 hours | 24 hours |
|---|---|---|---|---|---|---|---|
| phosphate (containing 0.1% SDS) buffer, pH 6.8 | Peak area | 4868.623 | 4864.179 | 4861.332 | 4865.548 | 4853.247 | 4837.464 |
| | Relative content | 100.0% | 99.9% | 99.9% | 99.9% | 99.7% | 99.4% |
| Water | Peak area | 3627.570 | 3623.876 | 3610.467 | 3602.525 | 3592.348 | 3590.479 |
| | Relative content | 100.0% | 99.9% | 99.5% | 99.3% | 99.0% | 99.0% |
| Water (containing 0.1% SDS) | Peak area | 5456.676 | 5443.102 | 5433.346 | 5430.342 | 5421.376 | 5422.712 |
| | Relative content | 100.0% | 99.8% | 99.6% | 99.5% | 99.4% | 99.4% |

The inventor studied the solution stability of the tablet prepared in Example 1 as example in 0.1 mol/L hydrochloric acid solution, acetate buffer (pH 4.5), phosphate buffer (pH 6.8), phosphate buffer containing 0.1% SDS (pH 6.8), water and water containing 0.1% SDS. According to the dissolution and release rate test (the second method described in general rule 0931 of volume IV of the Chinese Pharmacopoeia 2015 Edition) under a condition of 50 rpm, an eluate was taken at 30 minutes, and then filtered. The filtrate was used as the test solution to study the solution stability at room temperature within 24 hours. The solution stability data is shown in Table 4.

The results showed that the tablet prepared in the present invention was stable within 24 hours in 0.1 mol/L hydrochloric acid solution, acetate buffer (pH 4.5), phosphate buffer containing 0.1% SDS (pH 6.8), water and water containing 0.1% SDS; and the tablet degraded slightly in phosphate buffer (pH 6.8).

2. Stability Under Light, High Temperature or High Humidity Conditions

TABLE 6

Results of influencing factor study (study condition: high temperature)

| Study item | | Standard requirement | Storage condition: 40° C. — Amount for quality study at each storage point: 63 tablets — Storage time: 0 d | 40° C. 25 tablets 5 d | 40° C. 25 tablets 10 d | 40° C. 25 tablets 30 d | 60° C. 63 tablets 0 d | 60° C. 25 tablets 5 d | 60° C. 25 tablets 10 d | 60° C. 25 tablets 30 d |
|---|---|---|---|---|---|---|---|---|---|---|
| Liquid chromatography identification | | The retention time should be the same. | Same | Same | Same | Same | Same | Same | Same | Same |
| Dissolution rate (%) 15 min | | Should be ≥80 | 98 | 98 | 94 | 95 | 98 | 99 | 99 | 97 |
| Related substance (%) | Impurity A[2] | Should be ≤2.0 | 0.10 | 0.14 | 0.11 | 0.21 | 0.10 | 0.11 | 0.07 | 0.10 |
| | Other maximum single impurity | Should be ≤0.2 | 0.04 | 0.04 | 0.05 | 0.01 | 0.04 | 0.02 | 0.03 | 0.04 |
| | Total impurity | Should be ≤3.0 | 0.15 | 0.19 | 0.17 | 0.24 | 0.15 | 0.16 | 0.14 | 0.19 |
| Moisture (%) | | Should be ≤3.0 | 2.3 | 2.4 | 2.4 | 1.6 | 2.3 | 2.5 | 2.4 | 1.6 |
| Crystal form | | Should be the same as that at day 0 | Meet the requirement | / | Meet the requirement | Meet the requirement | Meet the requirement | / | Meet the requirement | Meet the requirement |
| Content (%) | | Should be 90.0 to 110.0 | 99.6 | 101.1 | 98.8 | 99.3 | 99.6 | 100.0 | 99.5 | 99.1 |

[2]Note:
the RRT of impurity A is about 1.23.

The structure of impurity A is as follows:

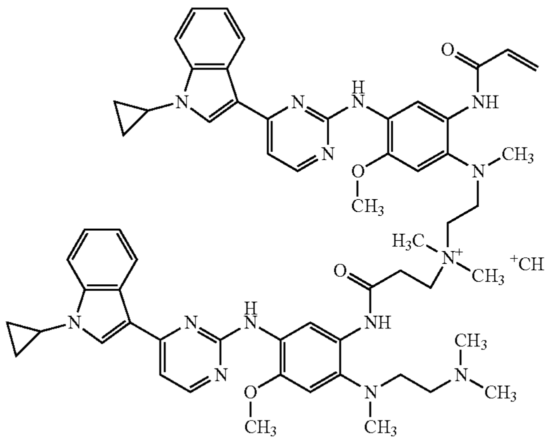

TABLE 7

| Results of influencing factor study (study condition: high humidity) | | | | | | |
|---|---|---|---|---|---|---|
| | | | Storage condition | | | |
| | | | 25° C./RH 75% (saturated sodium chloride solution) Amount for quality study at each storage point | | | |
| | | | 63 tablets | 25 tablets | 25 tablets | 25 tablets |
| | | Standard | Storage time | | | |
| Study item | | requirement | 0 d | 5 d | 10 d | 30 d |
| Liquid chromatography identification | | The retention time should be the same. | Same | Same | Same | Same |
| Dissolution (%) | | Should be ≥80 | 98 | 98 | 97 | 95 |
| Related substances (%) | Impurity A | Should be ≤2.0 | 0.10 | 0.16 | 0.09 | 0.21 |
| | Other maximum single impurity | Should be ≤0.2 | 0.04 | 0.04 | 0.04 | 0.01 |
| | Total impurity | Should be ≤3.0 | 0.35 | 0.19 | 0.13 | 0.25 |
| Moisture (%) | | Should be ≤3.0 | 2.3 | 3.7 | 3.5 | 3.9 |
| Crystal form | | Should be the same as that at 0 | Meet the requirement | / | Meet the requirement | Meet the requirement |
| Content (%) | | Should be between 90.0 and 110.0 | 99.6 | 101.3 | 99.6 | 99.6 |

TABLE 8

Results of influencing factor study (study condition: light)

| | | Standard requirement | Study item Storage condition Light Amount for quality study at each storage point: 310 tablets; Storage time: 0 d | 25 tablets; 5 d | 25 tablets; 10 d |
|---|---|---|---|---|---|
| Liquid chromatography identification | | The retention time should be the same | Same | Same | Same |
| Dissolution (%) | | Should be ≥ 80 | 98 | 98 | 97 |
| Related substance (%) | Impurity A | Should be ≤ 2.0 | 0.10 | 0.13 | 0.10 |
| | Other maximum single impurity | Should be ≤ 0.2 | 0.04 | 0.04 | 0.04 |
| | Total impurity | Should be ≤ 3.0 | 0.15 | 0.17 | 0.16 |
| Moisture (%) | | Should be ≤ 3.0 | 2.3 | 2.7 | 2.4 |
| Crystal form | | Should be the same as that at day 0 | Meet the requirement | / | Meet the requirement |
| Content (%) | | Should be between 90.0 and 110.0 | 99.6 | 101.2 | 98.7 |

The results are shown in Tables 6 to 8. The influencing factor study was conducted for 30 days (the study under light condition was conducted for 10 days, the total illumination was not less than 1.2×106 lux-hr). The results showed that the product was stable under light condition (total illuminance 1.2×106 lux/hr) without degradation, and there was no obvious change in various quality indicators. Under high temperature (40° C.), high temperature (60° C.) and 25° C./RH75% conditions, the related substance slightly degraded, but there was no obvious change in other quality indicators, and the sample had a good stability.

3. Product Stability

TABLE 9

Results of product quality study in the stability test (product of Example 1)

| Study item | | Limit requirement | Time: 0 day | 1 month | 2 months | 3 months |
|---|---|---|---|---|---|---|
| Appearance | | A light-yellow film-coated tablet, being from off-white to yellow after removing the coating | A light-yellow film-coated tablet, being off-white after removing the coating | A light-yellow film-coated tablet, being off-white after removing the coating | A light-yellow film-coated tablet, being off-white after removing the coating | A light-yellow film-coated tablet, being off-white after removing the coating |
| Dissolution (%) | | Should be ≥80 | 97 | 98 | 96 | 99 |
| Related substance (%) | Impurity A | Should be ≤2.0 | 0.11 | 0.17 | 0.19 | 0.18 |
| | Other maximum single impurity | Should be ≤0.2 | 0.08 | 0.06 | 0.06 | 0.06 |
| | Total impurity | Should be ≤3.0 | 0.44 | 0.38 | 0.45 | 0.46 |
| Content (%) | | Should be between 90.0 and 110.0 | 98.6 | 100.1 | 98.8 | 99.0 |

TABLE 10

| Results of product quality study in the stability test (product of Example 2) | | | | | | |
|---|---|---|---|---|---|---|
| Study item | | Limit requirement | Time: 0 day | 1 month | 2 months | 3 months |
| Appearance | | A pink film-coated tablet, being off-white to light yellow after removing the coating | A pink film-coated tablet, being off-white to light yellow after removing the coating | A pink film-coated tablet, being off-white to light yellow after removing the coating | A pink film-coated tablet, being off-white to light yellow after removing the coating | A pink film-coated tablet, being off-white to light yellow after removing the coating |
| Dissolution (%) | | Should be ≥80 | 98 | 99 | 97 | 99 |
| Related substances (%) | Impurity A | Should be ≤2.0 | 0.10 | 0.18 | 0.27 | 0.21 |
| | Other maximum single impurity | Should be ≤0.2 | 0.04 | 0.02 | 0.01 | 0.01 |
| | Total impurity | Should be ≤3.0 | 0.15 | 0.22 | 0.29 | 0.25 |
| Content (%) | | Should be between 90.0 and 110.0 | 99.6 | 99.7 | 100.9 | 100.6 |

It can be seen from Tables 9 and 10 that the tablet prepared in the present invention had a good quality, the product quality was stable in the stability test. The prescription and process of the product were stable, and the reproducibility was good. The samples prepared in other Examples all had similar stability results to those of the samples of Examples 1 and 2. Dissolution test and result analysis 1. Four batches of the product prepared in Example 1 were randomly selected for testing. The results are shown in Table 10.

Dissolution Test and Result Analysis

1. Four batches of the product prepared in Example 1 were randomly selected for testing. The results are shown in Table 10.

TABLE 11

| Dissolution curve of the product in 0.1 M hydrochloric acid medium (product of Example 1) | | | | | |
|---|---|---|---|---|---|
| Product of Example 1 | | Sample 1 | Sample 2 | Sample 3 | Sample 4 |
| Cumulative dissolution rate (%) | 5 min | 51 | 47 | 57 | 76 |
| | 10 min | 94 | 88 | 97 | 97 |
| | 15 min | 98 | 94 | 99 | 100 |
| | 30 min | 99 | 97 | 100 | 101 |
| | 45 min | 100 | 98 | 100 | 102 |

The results showed that the obtained samples all had good dissolution uniformity.

2. The dissolution test of the product prepared in Example 2 in different media was carried out. The results are shown in Table 12.

TABLE 12

| Dissolution data of the product in different media (product of Example 2) | | | | | |
|---|---|---|---|---|---|
| Dissolution medium | | 0.1 mol/L hydrochloric acidl | Buffer, pH 4.5 | Buffer containing 0.1% SDS, pH 6.8 | Water containing 0.1% SDS |
| Cumulative dissolution rate (%) | 5 min | 34 | 30 | 66 | 41 |
| | 10 min | 84 | 76 | 86 | 75 |
| | 15 min | 97 | 92 | 90 | 87 |
| | 30 min | 101 | 96 | 91 | 93 |
| | 45 min | 101 | 96 | 92 | 90 |
| | 60 min | 101 | 97 | 92 | 94 |

The results show that the product prepared in the present invention had good dissolution rate in different media.

The samples prepared in other Examples had similar dissolution profile to those of the samples of Examples 1 and 2.

What is claimed is:

1. A pharmaceutical composition, comprising a mesylate salt of N-(5-((4-(1-cyclopropyl-1H-indol-3-yl)pyrimidin-2-yl)amino)-2-((2-(dimethylamino)ethyl)(methyl)amino)-4-methoxyphenyl)acrylamide as an active ingredient, and at least one pharmaceutically acceptable excipient, wherein the pharmaceutical composition is a tablet and wherein the excipient comprises (a) fillers; wherein the fillers are microcrystalline cellulose and lactose;

the weight ratio of microcrystalline cellulose to lactose is 1:3 to 3:1;

the microcrystalline cellulose is microcrystalline cellulose KG802;

the microcrystalline cellulose KG802 is present in an amount of 30% to 50% by weight; and the lactose is present in an amount of 5% to 15% by weight;

(b) one disintegrant which is carboxymethyl starch sodium, and the disintegrant is present in an amount of 14% to 16% by weight;

(c) lubricants, wherein the lubricants are sodium stearyl fumarate and magnesium stearate, and wherein the active ingredient is present in an amount of 35% to 50% by weight.

2. The pharmaceutical composition according to claim 1, wherein the weight ratio of microcrystalline cellulose KG802 to lactose is 2-3:1.

3. The pharmaceutical composition according to claim 1, wherein the composition comprises:

35% to 50% by weight of mesylate salt of N-(5-((4-(1-cyclopropyl-1H-indol-3-yl)pyrimidin-2-yl)amino)-2-((2-(dimethylamino)ethyl)(methyl)amino)-4-methoxyphenyl)acrylamide;

5% to 15% by weight of lactose;

30% to 50% by weight of microcrystalline cellulose KG802;

14% to 16% by weight of carboxymethyl starch sodium; and 0.5% to 5% by weight of sodium stearyl fumarate and magnesium stearate.

4. The pharmaceutical composition according to claim 3, wherein the composition comprises:

43.3% by weight of mesylate salt of N-(5-((4-(1-cyclopropyl-1H-indol-3-yl)pyrimidin-2-yl)amino)-2-((2-(dimethylamino)ethyl)(methyl)amino)-4-methoxyphenyl)acrylamide;

10.2% by weight of lactose;

30.0% by weight of microcrystalline cellulose KG802;

14% by weight of carboxymethyl starch sodium; and 2.5% by weight of sodium stearyl fumarate and magnesium stearate.

5. A method for preparing the pharmaceutical composition according to claim 1, comprising the following steps:

(i) sieving microcrystalline cellulose KG 802, lactose, carboxymethyl starch sodium, sodium stearyl fumarate, and an active ingredient;

(ii) mixing the microcrystalline cellulose KG 802, lactose, carboxymethyl starch sodium, sodium stearyl fumarate, and the active ingredient to form a mixed powder;

(iii) granulating the mixed powder by dry granulation to form granules;

(iv) mixing the granules with magnesium stearate;

(v) compressing the mixture of the granules and magnesium stearate into a tablet; and (vi) optionally, coating the tablet, wherein the active ingredient is mesylate salt of N-(5-((4-(1-cyclopropyl-1H-indol-3-yl)pyrimidin-2-yl)amino)-2-((2-(dimethylamino)ethyl)(methyl)amino)-4-methoxyphenyl)acrylamide, the active ingredient is present in an amount of 35% to 50% by weight, the weight ratio of the microcrystalline cellulose KG802 to lactose is 1:3 to 3:1, the microcrystalline cellulose KG802 is present in an amount of 30% to 50% by weight, the lactose is present in an amount of 5% to 15% by weight, and the carboxymethyl starch sodium is present in an amount of 14% to 16% by weight.

6. The pharmaceutical composition according to claim 1, wherein a unit dose of the active ingredient is 10 mg to 200 mg.

7. The pharmaceutical composition according to claim 1, wherein the fillers are microcrystalline cellulose KG802 and anhydrous lactose.

8. The pharmaceutical composition according to claim 1, wherein the lubricants are present in an amount of 0.1% to 10% by weight.

9. The pharmaceutical composition according to claim 8, wherein the sodium stearyl fumarate is present in an amount of 0.1% to 5% by weight, and the magnesium stearate is present in an amount of 0.1% to 5% by weight.

10. The pharmaceutical composition according to claim 1, wherein a unit dose of the active ingredient is 55 mg to 110 mg.

11. The pharmaceutical composition according to claim 1, wherein the lubricants are present in an amount of 0.2% to 5% by weight.

12. The pharmaceutical composition according to claim 8, wherein the sodium stearyl fumarate is present in an amount of 0.3% to 3% by weight, and the magnesium stearate is present in an amount of 0.2% to 2% by weight.

13. The pharmaceutical composition according to claim 1, wherein the pharmaceutical composition is a coated tablet.

14. The pharmaceutical composition according to claim 1, wherein the pharmaceutical composition is an immediate-release film-coated tablet.

* * * * *